(12) United States Patent
Pearson (10) Patent No.: US 8,349,904 B2
(45) Date of Patent: Jan. 8, 2013

(54) PROCESS AND APPARATUS FOR THE PRODUCTION OF USEFUL PRODUCTS FROM CARBONACEOUS FEEDSTOCK

(75) Inventor: Stanley R. Pearson, Baton Rouge, LA (US)

(73) Assignee: Pearson Technologies, Inc., Aberdeen, MS (US)

( * ) Notice: Subject to any disclaimer, the term of this patent is extended or adjusted under 35 U.S.C. 154(b) by 0 days.

(21) Appl. No.: 13/368,596

(22) Filed: Feb. 8, 2012

(65) Prior Publication Data

US 2012/0142522 A1 Jun. 7, 2012

Related U.S. Application Data

(62) Division of application No. 10/568,403, filed on Feb. 13, 2006.

(51) Int. Cl.
*C07C 27/00* (2006.01)
(52) U.S. Cl. ........ 518/706; 518/702; 518/704; 518/713; 518/715
(58) Field of Classification Search .................. 518/706, 518/702, 704, 713, 715
See application file for complete search history.

(56) References Cited

U.S. PATENT DOCUMENTS

| | | | |
|---|---|---|---|
| 2,460,508 | A | 2/1949 | Johnson et al. |
| 2,649,468 | A | 8/1953 | Benedict et al. |
| 4,348,487 | A | 9/1982 | Goldstein et al. |
| 4,409,405 | A | 10/1983 | Lin et al. |
| 4,497,637 | A | 2/1985 | Purdy et al. |
| 4,603,679 | A | 8/1986 | Ogden |
| 4,609,679 | A | 9/1986 | Wood et al. |
| 4,675,344 | A | 6/1987 | Conway et al. |
| 4,752,622 | A | 6/1988 | Stevens |
| 4,825,013 | A | 4/1989 | Quarderer et al. |
| 4,872,886 | A | 10/1989 | Henley et al. |
| 4,913,842 | A | 4/1990 | Yoneoka et al. |
| 5,073,356 | A | 12/1991 | Guro et al. |
| RE35,377 | E | 11/1996 | Steinberg et al. |
| 5,763,716 | A | 6/1998 | Benham et al. |
| 5,767,165 | A | 6/1998 | Steinberg et al. |
| 6,028,119 | A | 2/2000 | Kokubu et al. |
| 6,191,174 | B1 | 2/2001 | Early et al. |
| 6,218,439 | B1 | 4/2001 | Kobayashi et al. |
| 6,232,352 | B1 | 5/2001 | Vidalin |

FOREIGN PATENT DOCUMENTS

GB 2139224 A 11/1984

OTHER PUBLICATIONS

Canadian Office Action dated Sep. 26, 2011 for corresponding Canadian Patent Application No. 2,535,721 (4 pgs.).
European Search Report dated Oct. 13, 2011 for corresponding European Patent Application No. 04781608.7 (6 pgs.).

*Primary Examiner* — Elvis O Price
(74) *Attorney, Agent, or Firm* — Timothy S. Westby; Porter Hedges LLP (57) ABSTRACT

A carbonaceous feedstock to alcohol conversion process in which carbon dioxide is removed from the syngas stream issuing from a feedstock reformer, to yield a carbon dioxide depleted syngas stream including hydrogen, carbon monoxide and methane. This carbon dioxide depleted syngas stream is then passed through a Fischer-Tropsch reactor ultimately yielding a mixed alcohol product which is preferably largely ethanol. The removed carbon dioxide stream is passed through a methane reformer along with methane, which is produced in or has passed through a Fischer-Tropsch reactor, to yield primarily carbon monoxide and hydrogen. The carbon monoxide and hydrogen stream from the methane reformer are passed through the alcohol reactor. Also disclosed are a unique catalyst, a method for controlling the content of the syngas formed in the feedstock reformer, and a feedstock handling system.

38 Claims, 4 Drawing Sheets

PROCESS AND APPARATUS FOR THE PRODUCTION OF USEFUL PRODUCTS FROM CARBONACEOUS FEEDSTOCK

CROSS-REFERENCE TO RELATED APPLICATIONS

This application is a divisional application which claims the benefit under 35 U.S.C. §121 of U.S. patent application Ser. No. 10/568,403, filed Feb. 13, 2006, the disclosure of which is hereby incorporated herein by reference.

STATEMENT REGARDING FEDERALLY SPONSORED RESEARCH OR DEVELOPMENT

Not applicable.

BACKGROUND

The present invention relates to the conversion of carbonaceous feedstock into useful products. The term "carbonaceous" as used herein includes not only organic matter that is part of the stable carbon cycle, but also fossilized organic matter such as coal, petroleum, and natural gas, and products, derivatives and byproducts thereof such as plastics, petroleum coke and the like. The first step in such processes is the gasification of the feedstock in a so-called "reformer" to a stream of hydrogen, carbon monoxide, carbon dioxide and methane. This stream is referred to as syngas, and its generation is disclosed in U.S. Pat. No. 4,872,886, and others. The '886 patent includes an oxidation first step, in which air is used to fire a portion of the feedstock. The resulting stream is then combined with a "coal slurry" stream in a second stage of the conversion reaction. U.S. Reissue 35,377 discloses the anaerobic reaction of the feedstock with steam.

The various ingredients in a stream of syngas can then be converted into other compounds in a so-called Fischer-Tropsch reactor. The catalyst used in the reactor, and to some extent the temperatures and pressures used, will determine what products can be obtained.

The Fischer-Tropsch reaction disclosed at the bottom of page 106 in *Organic Chemistry*, Third Edition, by Brewster and McEwen, ©1961 shows the conversion of carbon monoxide and hydrogen to alkanes over a cobalt-thoria catalyst. U.S. Pat. No. 4,752,622 discloses and claims the use of a three component catalyst comprising molybdenum or tungsten, cobalt or nickel, and an alkali or alkaline earth promoter, to produce methanol from carbon monoxide and hydrogen. U.S. Pat. No. 4,609,679 selectively catalyzes for the production of methane, by using ruthenium combined with tantalum, niobium, vanadium or mixtures thereof. U.S. Pat. No. 4,675,344 (Canadian CA 1,267,160) controls the ratio of methanol to higher alcohols produced by using molybdenum or tungsten sulfide catalysts, and adjusting the concentration of a sulfur releasing substance in the feed.

The conversion of methanol to ethanol and higher alcohols in the presence of carbon monoxide and hydrogen is disclosed in U.S. Pat. No. 4,825,013 and its Canadian counterpart CA 1,268,189. The patent claims achieving this conversion through the use of a heterogeneous catalyst comprised of molybdenum or tungsten and an alkali or alkaline earth element.

German Patent Application 32 42 697 A1 is directed towards a process for the concurrent production of methanol and ethanol by catalytically converting synthesis gas into methanol and separating the methanol from the reaction mixture. The separated methanol, along with excess gas remaining, is converted to ethanol at an increased pressure and an increased temperature, using a cobalt catalyst. In this process methanol, as well as ethanol, is produced from a single raw substance in a two-step process, using a heterogeneously catalyzed system with a homogeneously catalyzed system. Fresh synthesis gas is added if the excess gas does not contain enough carbon monoxide prior to homologization.

In European patent application 849,245, natural gas is converted in a reformer to a syngas stream of carbon monoxide, carbon dioxide, hydrogen and unconverted methane This entire syngas stream is passed through a Fischer-Tropsch reactor to produce methanol. The unreacted syngas is divided into a CO, $CO_2$ and $CH_4$ stream, which is recycled back through the reformer; and a hydrogen rich stream, which is combined with oxygen and combusted to provide heat for the reformer.

PCT patent application WO 82/02547 removes $CO_2$ from a syngas stream and recycles it through a reformer along with steam and an incoming stream of methane. The reactants produce a syngas stream from which the $CO_2$ is thus continuously removed and recycled.

European patent application 253,540 is exemplary of art in which higher alcohols are produced in a Fischer-Tropsch reactor from feedstock (coal slurry) syngas, and any methanol produced is recycled through the Fischer-Tropsch reactor.

SUMMARY

One aspect of the present invention comprises a carbonaceous feedstock to alcohol conversion process in which carbon dioxide is removed from the syngas stream issuing from a feedstock reformer, to yield a carbon dioxide depleted syngas stream including hydrogen, carbon monoxide and methane. This carbon dioxide depleted syngas stream is then passed through a Fischer-Tropsch reactor ultimately yielding a mixed alcohol product which is preferably largely ethanol. The removed carbon dioxide stream is passed through a methane reformer along with methane, which is produced in or has passed through a Fischer-Tropsch reactor, to yield primarily carbon monoxide and hydrogen. The carbon monoxide and hydrogen stream from the methane reformer are passed through the alcohol reactor.

Other aspects of the invention include, without limitation, a unique catalyst, a method for controlling the content of the syngas formed in the feedstock reformer, and a feedstock handling system. These and other features, advantages and aspects of the invention will be more fully understood and appreciated by reference to the written specification and appended drawings.

DETAILED DESCRIPTION

Introduction. The preferred embodiment apparatus employed is divided into three "Units" in FIG. 1. In Unit I, carbonaceous feedstock is converted to syngas 3, and carbon dioxide stream 8 is removed from the syngas stream 3 at acid gas removal apparatus 160. In Unit II, the carbon dioxide depleted syngas stream 5 is subjected to a Fischer-Tropsch reactor 220 resulting in a mixed alcohol product stream 5 Immediately subsequent thereto, carbon monoxide and hydrogen are removed via a gas liquid separator 225 and recycled as stream 9 back into the carbon dioxide depleted syngas stream 5 (which has been combined with stream 6, infra) Also in this gas liquid separation phase, methane is purged from the mixed alcohol product stream and the methane is subjected to the methane recycle reformer in Unit III as stream 13. The mixed alcohol product stream is subjected to a methanol distillation at 230. The methanol is removed from the mixed alcohol product stream and recycled as stream 10 back into the carbon dioxide depleted syngas stream 5, 6. After the methanol distillation, the remaining mixed alcohol product stream 11 is comprised largely of ethanol. In Unit III, carbon dioxide stream 8, methane stream 13 and steam are recycled through a methane reformer resulting in the production of carbon monoxide and hydrogen stream 6. Carbon monoxide and hydrogen stream 6 is blended with carbon dioxide depleted stream 5 and the combined stream 5, 6 is fed to the alcohol reactor 220.

Whereas prior art carbonaceous feedstock conversion processes yield about 424 liters (112 gallons) of ethanol per ton of feedstock, and prior art fermentation processes yield about 378 liters (100 gallons) of ethanol per ton of feedstock, the present alcohol production process yields 757 liters (200 gallons) or more of ethanol per ton of feedstock.

Unit I: The Feedstock Reformer (FR)

Figure 1:
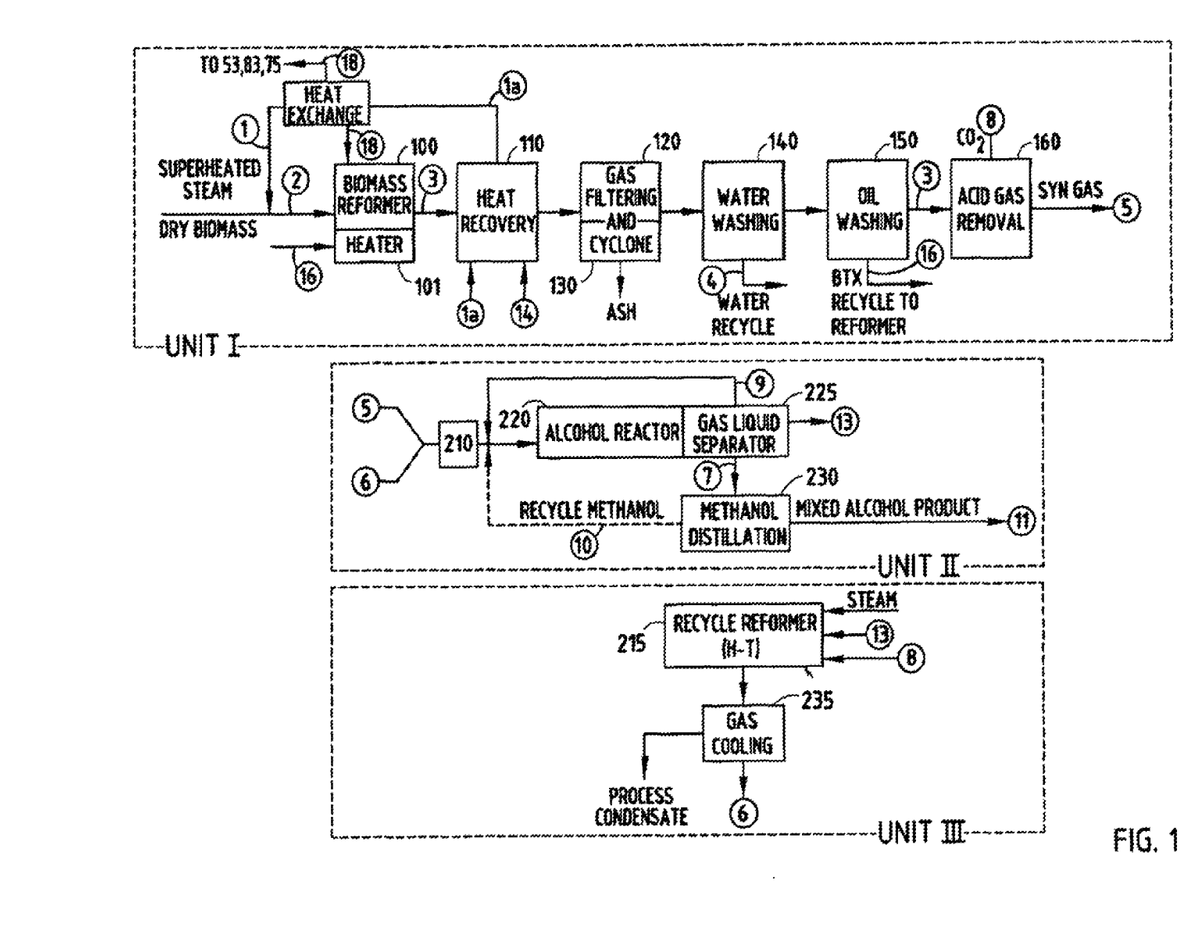
FIG. 1 is a process flow sheet identifying the basic operations conducted in a preferred embodiment of the invention.

In Unit I, feedstock 2 is anaerobically reformed in feedstock reformer 100 with superheated steam 1 into a syngas stream 3 comprising as its primary components hydrogen, carbon dioxide, carbon monoxide and methane. Minor amounts of other ingredients may be formed. Preparation of the feedstock prior to introduction into feedstock reformer 100 is illustrated in FIG. 3.

Figure 3:
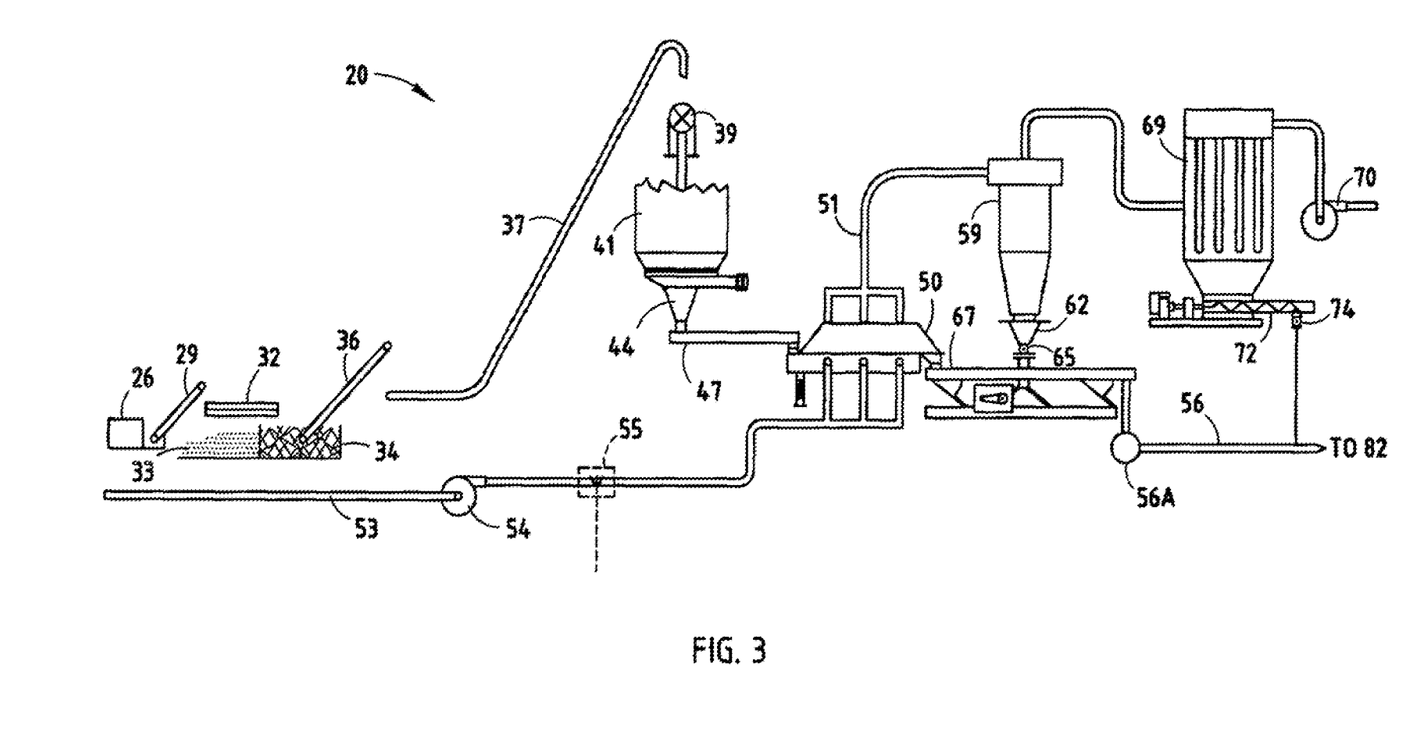
FIG. 3 is an illustration of the feedstock preparation apparatus.

Referring to FIG. 3, feedstock preparation apparatus 20 includes a rough grinder 26 which may be used depending on the consistency of feedstock. The feedstock is primarily wood and/or other organic material. Rough grinder 26 may be used if the feedstock is clumped together, in unusually large conglomerates, or if the feedstock needs to be further ground before being subjected to screen 32. After the feedstock is optionally subjected to rough grinder 26, feedstock is conveyed by first conveyor 29 to a position above screen 32. Feedstock falls off the first conveyor 29 to screen 32 where dirt 33 and iron are separated from feedstock. Iron removal is accomplished by appropriate placement of magnets. Feedstock is separated to a location 34 at the beginning of the second conveyor 36. Second conveyor 36 carries the feedstock to conveyor 37. Conveyor 37 carries feedstock to feed mill 39. Feed mill 39 comprises a grinder which grinds the feedstock to a size allowing it to pass through a 4.8 millimeter (3/16-inch) screen. After passing through the 4.8 millimeter (3/16-inch) screen, the feedstock falls into feed storage bin 41. For a plant having a feedstock feed rate of about 181 kilograms (400 lbs.) per hour, feed storage bin 41 is about 3 meters (10 feet) in diameter and about 3 meters (10 feet) tall. From feed storage bin 41, feedstock is placed in vibrating bin discharger 44. A vibrating dryer feed conveyor 47 then moves feedstock from vibrating bin discharger 44 to dryer 50, where the feedstock is dried to a moisture content of from about 5% to about 20%, more preferably about 9% to about 15%.

Flue gas inlet 53 feeds flue gas (stream 18 from the heat source of feedstock reformer 100) into wood dryer system 50. Flue gas inlet 53 may contain compressor 54 and/or fuel gas start-up combuster 55. Fuel gas up-start combuster 55 is usually not necessary. However, if the drier has been shut down, combuster 55 ignites a stream of fuel gas which is fed into the flue gas stream at combuster 55. Any fuel may be employed.

The flue gas is fed into dryer 50 and mixes with comminuted feedstock to dry it, purge it and heat it for further processing. The flue gas comprises about 80% nitrogen and 20% $CO_2$. From dryer 50 fines and smaller feedstock particles are carried by flue gas out through drier stack 51 to a cyclone separator 59, while larger feedstock particles pass along a vibrating screen at the bottom of dryer 50, out through one end thereof, where they are deposited on enclosed vibrating screen conveyor 67. Cyclone separator 59 separates the fines from the remaining smaller feedstock particles. The smaller feedstock particles flow down to dryer cyclone dust collector 62, and then pass from dryer cyclone dust collector 62 through solids outlet airlock 65, wherein the smaller particles of feedstock are then reunited with the larger particles of feedstock on vibrating screen feed conveyor 67.

Figure 4:
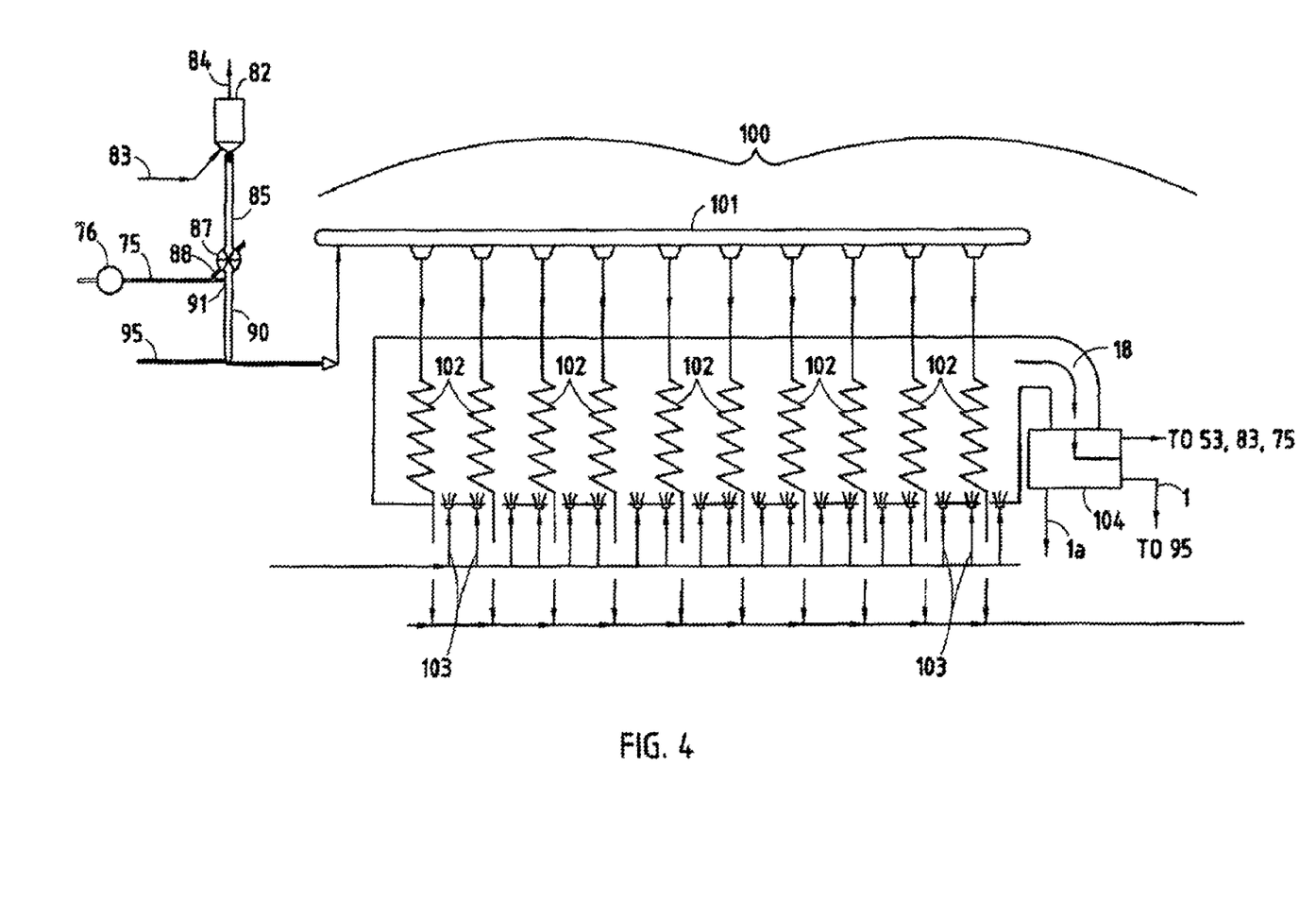
FIG. 4 is an illustration of the feedstock reformer.

The vibrating screen feed conveyor 67 conveys the dried feedstock to blower 56A, which blows the dried comminuted feedstock, along with the inert flue gas, through pipe 56. The use of flue gas as a "carrier" minimizes the introduction of air into the system. The dried feedstock particles are fed by blower 56A through feed pipe 56 to bunker 82 (FIG. 4). The fines of feedstock are then vented from separator 59 and carried to bag house dust collector 69. The fines are carried by the flue gas flow, induced in part by blower 70. The fines of feedstock which fall to the bottom of bag house dust collector 69 are fed via screw conveyor 72 through rotary airlock 74. They are fed into the flow of large and small particles of feedstock being carried via a flue gas in feed pipe 56.

Blower 70 and blower 54 are balanced so as to maintain a relatively neutral pressure in vibrating screen drier 50. There is just enough of a pressure difference to keep the flue gas flowing through drier 50.

Feedstock is fed via flue gas feed pipe 56, to feed hopper or bunker 82 (FIG. 4). A purge gas inlet 83 feeds flue gas into hopper 82. Being about 80% nitrogen and about 20% carbon dioxide, flue gas helps insure that the reformation process in reformer 100 will be carried out anaerobically. Hopper 82 also includes a vent 84 for venting flue gas.

Figure 5:
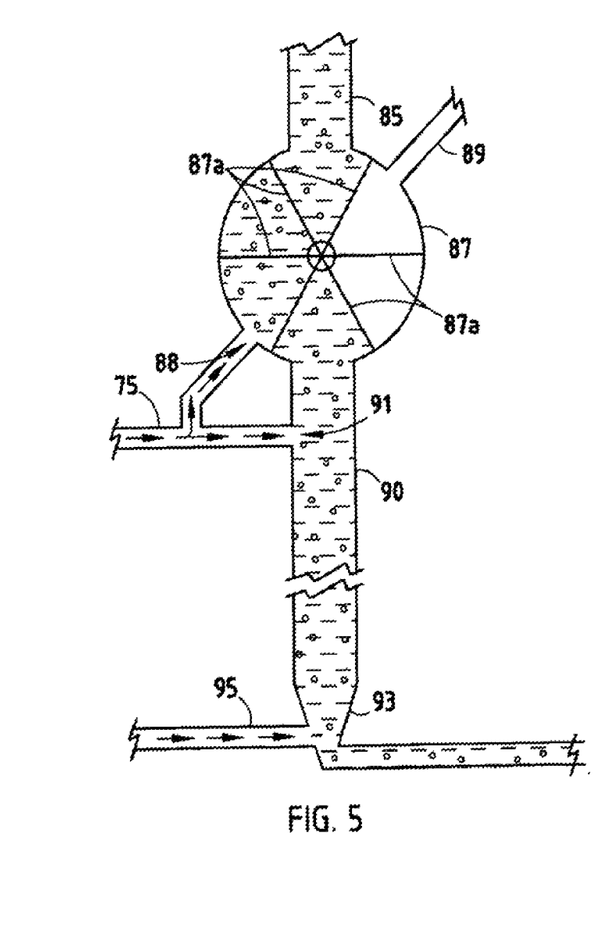
FIG. 5 is a cross-sectional view of the feedstock metering and steam mixing apparatus.

From hopper 82, feedstock settles into tube 85, which extends from the bottom of hopper 82. The feedstock is metered by rotary valve 87 into feed tube 90, at the bottom of which it is entrained with steam under pressure entering from steam line 95. To keep feedstock flowing into the stream of steam, and in order to counter steam back pressure in pipe 90, a supply of flue gas 18 is moved through line 75 via compressor 76 to inlet 91 near the top of feed tube 90 (FIGS. 4 and 5). To prevent the pressure in tube 90 from blowing feedstock back into rotary valve 87, some of the flue gas is also split off from line 75 and fed to inlet 88 of rotary valve 87. Rotary valve 87 includes a central rotor having a plurality of vanes 87a which divide the interior of valve 87 into separate compartments. Opposite inlet 88 on rotary valve 87, is outlet pressure vent 89. As the rotor of valve 87 rotates counterclockwise, the compartment formed by vanes 87a at the top fill with feedstock. That filled compartment is then rotated counterclockwise until it opens to inlet 88, where it is pressurized with incoming flue gas. As the rotor rotates further, the feedstock filled and pressurized chamber opens into feed tube 90. Since the pressure in the rotor chamber is equalized with the pressure in tube 90, the feedstock falls down into tube 90. As the valve rotor continues on its counterclockwise journey, it is eventually vented through vent 89, such that when the chamber reaches feed tube 85 again, it is depressurized and will not vent back up into feed tube 85. After feedstock has moved through rotary valve 87 and into feed tube 90, it feeds by gravity into mixing chamber 93 at the bottom of tube 90, where superheated steam 510° C. (950° F. steam) from steam line 95 is mixed with feedstock.

Superheated steam carries the feedstock to feedstock reformer 100 (FIG. 4). In the process of heating up the feedstock, the steam cools to approximately 204° C. (400° F.) as the superheated steam and feedstock approach wood reformer 100. Within feedstock reformer 100 a flow divider 101 distributes the cooled steam and feedstock into about 76 millimeters (3-inch) diameter tubing coils 102 through which steam and feedstock pass. Feedstock reformation carried out in feedstock reformer 100 is endothermic. Heat for the feedstock reformation process is provided by burners 103 at the bottom of feedstock reformer 100. Excess syngas or any other fuel can be burned in burners 103 at the bottom of reformer 100. The flue gas 18 from burners 103 passes through a heat exchanger 104, used to help superheat the incoming stream of water 1a to superheated steam 1, and then into flue gas lines 53, 83 and 75 (FIG. 4). For greater energy independence of the overall process, even more excess syngas can be made and used to run a turbine and generate electricity to power the compressors and other electrically driven devices.

The inlet temperature of the feedstock and superheated steam 1 entering feedstock reformer 100 is about 204° C. (400° F.) The exit temperature of the syngas leaving feedstock reformer 100 is between 871° C. (1600° F.) and 1204° C. (2200° F.), preferably about 898° C. (1650° F.) to about 926° C. (1700° F.) At 1093° C. (2000° F.) and above, with a contact time of 5.0 seconds, one obtains less than one mole percent of methane and a great deal of $CO_2$, which is an undesirable result. Pressure in feedstock reformer 100 does not appear to be critical. The reformer is preferably run at a pressure of about 241 kilopascal (KPa) (35 psig) to about 276 KPa (40 psig).

Figure 2:
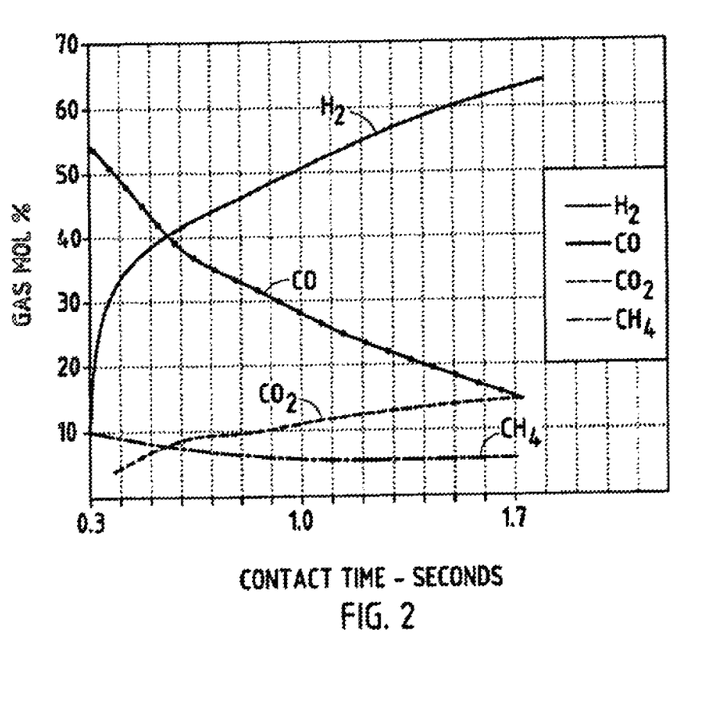
FIG. 2 is a graph illustrative of the variation in syngas products which one achieves as a function of the temperature, contact time of the gas in the feedstock reformer, the ratio of hydrogen, carbon and oxygen in the feedstock used and the ratio of steam to feedstock fed to the reformer.

For any given feedstock, one can vary the proportions of hydrogen, carbon dioxide, carbon monoxide and methane which are contained in the resulting syngas stream as a function of contact time in the reformer, temperature at exit, the amount of steam introduced, and to a lesser extent, pressure (FIG. 2). Certain proportions of syngas components are better than others for producing alcohols, while other proportions are preferred for producing alkanes. Generally speaking, if one wants to produce alkanes, one prefers a syngas stream containing more carbon monoxide and methane relative to hydrogen than is desired when one wishes to produce ethanol or methanol.

FIG. 2 graphs the approximate syngas content as a function of contact time for a feedstock converter run on wood, with an exit gas temperature of 898° C. (1650° F.) to 926° C. (1700° F.) Water content and the mole percents of other constituents in the gas are not shown in FIG. 2. Ninety-nine percent conversion occurs at 0.4 seconds. As can be seen, as contact time increases, the amount of hydrogen obtained increases, the amount of carbon monoxide decreases, the amount of carbon dioxide increases, and the amount of methane decreases slightly. By adjusting the contact time, one can optimize these ingredients for the production of alcohols. Generally speaking, one wants a contact time of from about 0.4 seconds to about 5.0 seconds, with from about 1.0 seconds to about 3.0 seconds being preferred for the production of ethanol. It is most preferable to operate at an exit temperature of about 898° C. (1650° F.) to about 926° C. (1700° F.) with about 1.0 seconds to about 2.0 seconds contact time in the reformer. Contact time is calculated by dividing the internal volume of the reformer by the flow rate of the syngas exiting the reformer.

FIG. 2 would, of course, look different for different feedstock, as well as different amounts of steam and different operating temperatures and pressures.

The amount of superheated steam 1 used is a function of the nature of the feedstock used. Steam provides the additional hydrogen necessary to maximize alcohol production from the feedstock. In terms of the carbon to hydrogen stoichiometric ratio in lower alcohols such as methanol and ethanol, dry feedstock typically has a stoichiometric excess of carbon relative to hydrogen. Thus water, either trapped in the feedstock or in the form of superheated steam, or both, provides additional hydrogen to maximize alcohol production. Preferably, the feedstock is relatively dry, and the water necessary is provided in the form of added superheated steam. For making alcohol from wood feedstock, one preferably uses from about 0.14 kilograms (0.3 pounds) to about 0.18 kilograms (0.4 pounds) of steam per pound of "dry" feedstock. Since the "dry" feedstock in our process contains about 9% to about 15% moisture, one has a total water to wood ratio of about 0.4 to 0.5. This results in a fairly efficient operation.

Exemplary feedstock which can be used include: lignite, coal, red cedar, southern pine, hardwoods such as oak, cedar, maple and ash, bagasse, rice hulls, rice straw, kennaf (a weed), sewer sludge, motor oil, oil shale, creosote, pyrolysis oil from a tire pyrolysis plant, old railroad ties, dried distiller grains, corn stalks and cobs, animal excrement, and straw. The hydrogen and oxygen content for various different wood materials are shown in Table 1 below:

TABLE 1

| Type | Red Oak Sawdust | | Fir Mill Waste | | Furniture Waste | | Hybrid Poplar | | Alder/Fir Sawdust | |
|---|---|---|---|---|---|---|---|---|---|---|
| | As Rec'd | Dry | As Rec'd | Dry | As Rec'd | Dry | As Rec'd | Dry | As Rec'd | Dry |
| Carbon | 44.24 | 49.96 | 18.95 | 51.23 | 43.85 | 49.87 | 46.72 | 50.18 | 24.17 | 51.02 |
| Hydrogen | 5.24 | 5.92 | 2.21 | 5.98 | 5.2 | 5.91 | 5.64 | 6.06 | 2.75 | 5.8 |
| Oxygen (Note 1) | 38.76 | 43.77 | 15.66 | 42.29 | 35.42 | 40.29 | 37.66 | 40.44 | 18.25 | 38.54 |
| Nitrogen | 0.03 | 0.03 | 0.02 | 0.06 | 0.25 | 0.29 | 0.56 | 0.6 | 0.22 | 0.46 |
| Sulfur | <0.01 | 0.01 | 0.01 | 0.03 | 0.03 | 0.03 | 0.02 | 0.02 | 0.02 | 0.05 |
| Ash | 0.28 | 0.31 | 0.15 | 0.41 | 3.18 | 3.61 | 2.51 | 2.7 | 1.96 | 4.13 |
| Moisture | 11.45 | — | 63.00 | — | 12.07 | — | 6.89 | — | 52.63 | |
| TOTAL | 100.00 | 100.00 | 100.00 | 100.00 | 100.00 | 100.00 | 100.00 | 100.00 | 100.00 | 100.00 |

Note 1:
Oxygen is not analyzed for in the sample. It is calculated by difference.

Similar information is provided for several other feedstock in Table 2, except that the hydrogen and oxygen content is expressed on a "per carbon" basis:

TABLE 2

Chemical composition of raw materials

| Raw materials | wt % maf[a] | H/C | O/C (wt % mf[b]) | Ash |
|---|---|---|---|---|
| Birch wood | 48.4 | 0.12 | 0.95 | 0.2 |
| Bagasse | 47.3 | 0.13 | 0.98 | 1.6 |
| Olive wastes | 49.5 | 0.13 | 0.88 | 2.1 |
| *Miscanthus* pellets | 48.9 | 0.09 | 0.96 | 2.4 |
| Straw pellets | 47.0 | 0.13 | 0.99 | 6.2 |

[a] maf: moisture and ash-free material.
[b] mf: moisture-free material.

Reaction (1) is an illustrative assumption of the feedstock conversion reaction:

$$C_4H_6O_2 + C_4H_6O_3 + H_2O \rightarrow H_2 + CO + CO_2 + CH_4 \quad (1)$$

The foregoing is, of course, merely illustrative, and is not expressed quantitatively. Those skilled in the art will appreciate that the actual hydrocarbon analysis for wood may vary significantly from this approximation. The quantitative content of the syngas stream will be determined as a function of feedstock used, quantity of steam used, reformation temperature and contact time in the reformer, as discussed above in connection with FIG. 2.

Syngas stream 3 passes from feedstock reformer 100 through a heat exchanger 110, where water 1a is preheated. The preheated water/steam then passes through heat exchanger 104, where it is further heated by flue gas from reformer 100 and becomes a stream of superheated steam 1 at a temperature of from about 454° C. (850° F.) to about 510° C. (950° F.) It is this superheated steam which is combined with feedstock stream 2 and is fed into feedstock reformer 100.

From heat exchanger 110, syngas stream 3 passes through a gas filtering device 120 and a cyclone 130, both of which are used to remove ash from syngas stream 3. Syngas stream 3 is then further washed and cooled with water in water washing unit 140. Water washing unit 140 comprises a column which is packed with conventional packing materials such as copper tubing, pall rings, metal mesh or other inert materials. Syngas stream 3 passes upwardly through the water washing column while water flows down through the upcoming syngas stream. The water wash serves to further cool syngas stream 3 to ambient temperature, and to remove any ash which may escape filter 120 and cyclone 130, though there should be no ash present unless there has been a rip in the filter bags of filter 120. Water from water washing unit 140 is recycled as stream 4. Stream 4 is de-gassed, filtered and passed through a carbon bed to remove organics. The water is then ready for re-use as needed in the system.

The syngas stream 3 at near ambient temperature passes through an oil-washing column 150. Column 150 is packed with conventional packing materials such as copper tubing, pall rings, metal mesh or other inert materials. Syngas stream 3 passes upwardly through oil washing column 150 while C-20 petroleum oil flows down through the upcoming syngas stream to remove any benzene, toluene, xylene or heavier hydrocarbons which may have been produced in feedstock reformer 100. The oil, benzene, toluene, xylene and heavier hydrocarbons exiting oil-washing column 150 are recycled as stream 16 through feedstock reformer 100.

Stream 3 then passes through an amine-scrubbing unit 160, which removes carbon dioxide from syngas stream 3. In this process the syngas is scrubbed with an amine based solvent in an absorption column A pressure swing adsorbent (PSA) unit, discussed below in connection with hydrogen removal, could be used instead of an amine scrubber to remove the carbon dioxide. The solvent is regenerated in a second column thereby releasing a high purity $CO_2$ product. The carbon dioxide passes as stream 8 to Unit IV. Syngas stream 5, with the carbon dioxide removed, then passes on to Unit II.

Unit II: Ethanol Production

In Unit II, carbon dioxide depleted syngas stream 5, and syngas stream 6 from recycle reformer Unit III are passed over scavenger beds 210, commonly referred to in the art as "guard cat beds," which remove any chlorine, sulfur or heavy hydrocarbon impurities from syngas streams 5 and 6. Exemplary materials which can be used in beds 210 include activated carbon to remove hydrocarbons, zinc oxide to remove sulfur, and silica gel to remove chlorides.

Streams 5 and 6 then pass to ethanol catalyzed Fischer-Tropsch reactor 220, at a pressure of between 12,410 KPa (1800 psi) and 16,547 KPa (2400 psi). Stream 5, 6 is joined by recycling carbon monoxide and hydrogen stream 9 from the gas liquid separator 225 and methanol stream 10 from the methanol distillation unit 230. The combined stream is fed to ethanol catalyzed Fischer-Tropsch reactor 220. Syngas stream 5, 6 is fed under pressure via compressor and all lines are equipped with back pressure values to make certain that there is no back flow into the respective lines.

Fischer-Tropsch reactor 220 comprises a series of stainless steel tubes, each approximately 25 millimeters (1-inch) to 51 millimeters (2-inches) in inside diameter. The tubes are loaded with a catalyst which favors the product of ethanol. Larger diameter tubes give more production capacity, but also allow for the generation of more heat, which it is deleterious to the catalyst. Thus, the tube diameter is usually selected as a compromise between flow through capacity desired and the ease with which the heat can be controlled.

The production of ethanol generates considerably more heat than does the production of methanol. One has to remove about 2.6 times as much heat from an ethanol catalyzed Fischer-Tropsch reactor as from a Fischer-Tropsch reactor catalyzed to produce methanol.

The threshold temperature for ethanol production is about 250° C. at the pressures at which the reactor operates. The ethanol reactor operates at from about 300° C. to about 380° C., and a pressure of from about 12,410 KPa (1800 psi) to about 16,547 KPa (2400 psi). Preferably, the reactor operates at no more than about 320° C., because the copper present in the catalyst sinters at about 350° C. to about 375° C. Running the reactor at above about 320° C. reduces the life of the catalyst. The gas hourly space velocity of the ethanol reactor is between 8,000 per hour and 50,000 per hour.

In the ethanol catalyzed Fischer-Tropsch reactor 220, a great deal of heat is generated which must be removed from the interior of the reactor to keep it from overheating. In the preferred embodiment, heat is removed and temperature controlled within the reactor by introducing a C-20 petroleum oil directly into the reactor tubes. Jacket cooling can be employed in addition or as an alternative, but direct oil cooling is preferred. The oil passing through the reaction tube of the reactor is cooled by removing it from the reactor and passing it through a heat exchanger where it boils water to create steam for use as needed in the system. The gaseous reactants and reaction products are passing through the oil as it is pumped through the reactor.

A unique ethanol catalyst is employed in the preferred embodiment. It consists essentially of elemental cobalt as its primary constituent, with minor amounts of manganese, zinc, copper, chromium and/or aluminum, and an alkali or alkaline earth promoter, with potassium carbonate being preferred for economic reasons. Preferably, it comprises on a metal elemental basis ex binder from about 65% to about 75% elemental cobalt, about 4% to about 12% manganese, about 4% to about 10% zinc, about 4% to about 6% copper, about 6% to about 10% chromium and/or about 6% to about 10% aluminum.

While the catalyst as used consists primarily of the above elements in their elemental form, the catalyst begins as a mixture of metal salts. Nitrates or carbonates are typically used. The catalyst goes through a "conditioning" process. In the conditioning process, the salts are largely reduced to their metallic elements, with some oxides remaining to form a lattice structure referred to as "spinels." The spinels help give the catalyst its overall spatial structure.

The catalyst may be used in its "pure" (or concentrated) form, or it may be diluted with carbon, by loading onto carbon pellets. The latter is often referred to as a supported catalyst. A pure catalyst will tend to run hotter than a support catalyst, creating a process cooling challenge. On the other hand, a more pure catalyst will be more active and hence can be used at lower reaction temperatures. If lower reaction temperatures can be used, the catalyst will last longer. Thus, a compromise must often be reached between the desirability of using a more active catalyst and the need to dilute it somewhat in order to facilitate temperature control.

To prepare the catalyst for use in its pure form, the salts in appropriate proportions are combined with about 3% to about 4% by weight of a binder and about ¼% to about ¾% lubricant. The salts, binder and lubricant mixture are pelletized in a pelletizer—basically a tableting machine—where pellets about 4 millimeters to about 6 millimeters in diameter and about 6 millimeters to about 10 millimeters in length are pressed at approximately 262,000 KPa (38,000 psi). The pellets are then calcined by heating them at a rate of about 60° C. per 10 minutes, to a temperature of around 450° C., where they are held for about two hours under a nitrogen blanket. The pellets are then allowed to cool, prior to conditioning.

A supported catalyst is prepared by immersing carbon pellets in a solution of the catalyst salts in appropriate proportions. The surface area of the carbon pellets is typically around 1200 square meters per gram. The water is evaporated off to leave catalyst loaded pellets. This process may have to be repeated to obtain the desired ratio of catalyst to carbon pellet. The catalyst loaded carbon pellets typically comprise from about 20% to about 40% catalyst. The catalyst loaded pellets need to be small enough to be packed into the reaction tubes. One wants to avoid dust, because it packs and clogs the tubes. Preferably, the pellets are from about 2 millimeters to about 4 millimeters in diameter, and from about 4 millimeters to about 10 millimeters long. Either the pure catalyst pellets or the catalyst loaded carbon pellets must then be conditioned before being used. The conditioning process involves passing reducer-doped nitrogen over beds of the pellets. Initially, one begins with nitrogen doped with about 1% hydrogen. The doped gas is preheated to about 200° C., and as it passes over the catalyst bed, a reduction process is initiated which is exothermic and causes the reaction bed to heat to about 400° C. The reaction is initially carried on at a pressure of about 172 KPa (25 pounds per square inch (psig)) to about 207 KPa (30 psig).

As the process proceeds, one measures the bed temperature and the gas temperature. As the temperature falls off, one adds additional amounts of hydrogen, building up to a level of about 25% to about 30% hydrogen. Pressure is also gradually increased over time, until it reaches about 5515 KPa (800 psi) to about 16,547 KPa (2400 psi). After additional hydrogen ceases to be effective in maintaining temperature, carbon monoxide is added to the reaction stream. Syngas can be used as a source of carbon monoxide. Some of the hydrogen is replaced with the syngas or carbon monoxide stream. The entire process takes days to complete.

The conditioned catalyst pellets are then cooled and put into drums under an inert gas purge, e.g., a nitrogen blanket. One cannot allow air to get to the catalyst. It is important that the catalyst be substantially free of oxygen. To the extent oxygen is contained in the catalyst, it reacts with hydrogen in the ethanol reactor and releases a great deal of excess and unwanted heat. Temperatures can rise to as high as about 1600° C.

It has been found that the present method produces about 0.11 kilograms (0.25 pounds) to about 0.14 kilograms (0.30 pounds) of ethanol per hour per pound of catalyst.

A number of reactions occur in ethanol catalyzed reactor 300, with the primary reactions being as follows:

$$2CO+H_2+CH_3OH \rightarrow C_2H_5OH+CO_2 \quad (2)$$

$$CO+2H_2+CH_3OH \rightarrow C_2H_5OH+H_2O \quad (3)$$

$$2CH_3OH \rightarrow C_2H_5OH+H_2O \quad (4)$$

$$CO+2H_2 \leftrightarrow CH_3OH \quad (5)$$

$$CO+H_2O \leftrightarrow CO_2+H_2 \quad (6)$$

$$2CO+2H_2 \leftrightarrow CH_4+CO_2 \quad (7)$$

$$CO+3H_2 \leftrightarrow CH_4+H_2O \quad (8)$$

The reactions of primary importance are reactions (2)-(5). Reactions (2)-(4) are important because they form ethanol. Reaction (5) forms methanol, some of which reacts in reactions (2), (3) and (4), and some of which is recycled from the alcohol distillation. Reactions (7) and (8) take place to some extent, requiring ultimately some conversion of methane to carbon monoxide and hydrogen in the methane and carbon dioxide reformer (also referred to as the recycle reformer), though some methane may be recycled to the feedstock reformer to minimize the ongoing generation of methane in the feedstock reformer.

The catalyst is designed to form ethanol and methanol in the ethanol reactor. It is desirable to have methanol present in stoichiometric excess, as it tends to drive the reactions towards production of ethanol. Some higher alcohols and some alkanes are also formed. Carbon dioxide and methane are also formed in ethanol reactor. Small amounts of methyl and ethyl formate are also formed in an equilibrium reaction.

The reaction products from ethanol reactor pass to a gas/liquid cooling and separation unit 225. Here, the alcohols are cooled to liquids and are separated from the gaseous elements, hydrogen, carbon dioxide, carbon monoxide and methane. The alcohols pass as stream 7 to methanol distillation unit 230.

The gas/liquid cooling and separation unit 225 comprises two coolers. One is a cross exchange unit and one is a water-cooling tower. The cooled liquid/gas stream passes to a gas/liquid separator, with the liquid being passed as stream 7 to the distillation column and the gas stream being either recycled back through alcohol reactor 220 as stream 9, or being diverted to methane reformer 215 in Unit III as stream 13. The gas coming from reactor 220 comprises unreacted carbon monoxide, unreacted hydrogen, carbon dioxide, and methane, in varying quantities. The methane content is monitored, and when the methane content is low, the gas is recycled through reactor 220 as stream 9. When the methane content gets to about 30%, gas stream 9 is diverted and sent as gas stream 13 to recycle reformer 215 in Unit III.

Unit III: Methane and $CO_2$ Recycle Reformer

When unreacted methane from feedstock reformer 100, and methane formed in Fischer-Tropsch reactor 220 reaches about 30% of the content of recycle stream 9, the gas stream is diverted and sent as gas stream 13 into the recycle reformer 215, along with the $CO_2$ as stream 8 issuing from acid gas removal apparatus 160. Steam is also fed into recycle reformer 215. Recycle reformer 215 is constructed in a standard manner In reformer 215, the methane component is reacted with $CO_2$ in the presence of a passivated catalyst. The reaction is carried on at 843° C. (1550° F.) to 898° C. (1650° F.).

The reaction products from the methane reformer primarily include carbon monoxide and hydrogen. These reaction products proceed to gas cooling unit 235. The products are cooled and the carbon monoxide and hydrogen are separated from unreacted water. The recovered water is recycled and converted into superheated steam. The carbon monoxide, hydrogen (and excess methane) are reintroduced as stream 6 into syngas stream 5 issuing from Unit I.

Of course, it is understood that the foregoing are merely preferred embodiments of the invention and that various changes and alterations can be made without departing from the spirit and broader aspects of the invention.

The invention claimed is:

1. A method for converting carbonaceous feedstock to alcohol comprising:
   reforming feedstock into a first syngas stream comprising hydrogen, carbon dioxide and carbon monoxide;
   separating the carbon dioxide from said first syngas stream, to yield a second syngas stream comprising hydrogen and carbon monoxide, from which carbon dioxide has been substantially removed;
   passing said second syngas stream through a catalyzed reactor to produce alcohol;
   diverting methane produced in said process to a methane reformer along with carbon dioxide, to produce carbon monoxide and hydrogen;
   passing said hydrogen and carbon monoxide from said methane reformer through said catalyzed alcohol reactor.

2. The process of claim 1 in which methane produced in said process is allowed to recycle back through said alcohol reactor with unreacted hydrogen and carbon monoxide;
   except that at least some of the time, at least a portion of said unreacted hydrogen, unreacted carbon monoxide and methane is diverted to said methane reformer.

3. The process of claim 2 in which said alcohol reactor is catalyzed to optimize ethanol production.

4. The process of claim 3 in which said catalyzed reactor is catalyzed by a catalyst consisting essentially of elemental cobalt as its primary constituent, with minor amounts of manganese, copper, zinc and one of chromium, aluminum and mixtures thereof.

5. The process of claim 4 in which the catalyst additionally includes an alkali or alkaline earth promoter.

6. The process of claim 5 in which the catalyst consists essentially of from about 65% to about 75% elemental cobalt, about 4% to about 12% manganese, about 4% to about 6% copper, about 4% to about 10% zinc, and about 6% to about 10% of one of chromium, aluminum or mixtures thereof.

7. The process of claim 4 in which said catalyst used consists essentially of from about 65% to about 75% elemental cobalt, about 4% to about 12% manganese, about 4% to about 6% copper, about 4% to about 10% zinc, and about 6% to about 10% of one of chromium, aluminum or mixtures thereof.

8. The process of claim 1 in which said catalyzed reactor is catalyzed by a catalyst consisting essentially of elemental cobalt as its primary constituent, with minor amounts of manganese, copper, zinc and one of chromium, aluminum and mixtures thereof.

9. The process of claim 8 in which the catalyst additionally includes an alkali or alkaline earth promoter.

10. The process of claim 9 in which the catalyst consists essentially of from about 65% to about 75% elemental cobalt, about 4% to about 12% manganese, about 4% to about 6% copper, about 4% to about 10% zinc, and about 6% to about 10% of one of chromium, aluminum or mixtures thereof.

11. The process of claim 8 in which said catalyst used consists essentially of from about 65% to about 75% elemental cobalt, about 4% to about 12% manganese, about 4% to about 6% copper, about 4% to about 10% zinc, and about 6% to about 10% of one of chromium, aluminum or mixtures thereof.

12. The process of claim 1 in which said step of reforming said carbonaceous feedstock is conducted at elevated temperature in a feedstock reformer, and includes adjusting the contact time of the syngas at elevated temperatures in the reformer, and adjusting the exit gas temperature of the syngas as it leaves the reformer, to achieve proportions of carbon monoxide, hydrogen and methane most closely approximating those desired given the intended use of the syngas.

13. The process of claim 12 which includes introducing said feedstock and superheated steam into the feedstock reformer at about 204° C. (400° F.);
   adjusting said exit temperature of said syngas leaving said feedstock reformer to between about 871° C. (1600° F.) and about 1204° C. (2200° F.);
   adjusting said contact time of said syngas within said reformer within a range of from about 0.4 seconds to about 5.0 seconds.

14. The process of claim 13 in which said syngas exit temperature and contact time are adjusted to produce a syngas most optimally proportioned to produce lower alcohols, by adjusting said syngas exit temperature to from about 898° C. (1650° F.) to about 926° C. (1700° F.), and said contact time from about 1.0 seconds to about 3.0 seconds.

15. The process of claim 14 in which said contact time is adjusted to from about 1.0 seconds to about 2.0 seconds.

16. The process of claim 13 in which said catalyzed reactor is catalyzed by a catalyst consisting essentially of elemental cobalt as its primary constituent, with minor amounts of manganese, copper, zinc and one of chromium, aluminum and mixtures thereof.

17. The process of claim 16 in which the catalyst additionally includes an alkali or alkaline earth promoter.

18. The process of claim 17 in which the catalyst consists essentially of from about 65% to about 75% elemental cobalt, about 4% to about 12% manganese, about 4% to about 6% copper, about 4% to about 10% zinc, and about 6% to about 10% of one of chromium, aluminum or mixtures thereof.

19. The process of claim 16 in which said catalyst used consists essentially of from about 65% to about 75% elemental cobalt, about 4% to about 12% manganese, about 4% to about 6% copper, about 4% to about 10% zinc, and about 6% to about 10% of one of chromium, aluminum or mixtures thereof.

20. The process of claim 12 in which said catalyzed reactor is catalyzed by a catalyst consisting essentially of elemental cobalt as its primary constituent, with minor amounts of manganese, copper, zinc and one of chromium, aluminum and mixtures thereof.

21. The process of claim 20 in which the catalyst additionally includes an alkali or alkaline earth promoter.

22. The process of claim 21 in which the catalyst consists essentially of from about 65% to about 75% elemental cobalt, about 4% to about 12% manganese, about 4% to about 6% copper, about 4% to about 10% zinc, and about 6% to about 10% of one of chromium, aluminum or mixtures thereof.

23. The process of claim 20 in which said catalyst used consists essentially of from about 65% to about 75% elemental cobalt, about 4% to about 12% manganese, about 4% to about 6% copper, about 4% to about 10% zinc, and about 6% to about 10% of one of chromium, aluminum or mixtures thereof.

24. The process of claim 1 in which said step of reforming feedstock into a first syngas stream includes:
comminuting the feedstock;
entraining the comminuted feedstock in a stream of inert gas and conveying it to a feed hopper where it is maintained in an inert gas environment;
metering the flow rate of feedstock into said reformer by a rotary valve through which the feedstock is fed, said rotary valve comprising a plurality of separate compartments which rotate from a valve inlet at which comminuted feedstock is fed into a valve compartment, to a valve outlet at which comminuted feedstock flows from said rotary valve;
feeding said feedstock through a feed conduit leading from said rotary valve outlet to a stream of steam under pressure into which the feedstock is fed and entrained;
feeding inert gas into said feed conduit under pressure, to prevent the steam under pressure from creating a back pressure in said feed conduit which would prevent comminuted feedstock from feeding into said stream of steam under pressure;
feeding inert gas under pressure into said rotary valve such that it pressurizes a compartment after it has passed said rotary valve inlet and before it has reached said rotary valve outlet whereby the comminuted feedstock contained in said compartment is maintained under pressure;
providing a vent in said rotary valve at a point between said outlet and said inlet, in the direction in which said compartments are rotated, such that a compartment under pressure which has been emptied at said outlet and is returning to said inlet will be vented of pressure introduced when said inert gas is fed into said compartment under pressure, before the emptied compartment reaches said rotary valve inlet;
feeding the steam entrained stream of comminuted feedstock to a feedstock reformer.

25. The process of 24 in which said comminuted feedstock is dried to a moisture content of from about 5% to about 20% before being fed into said feed hopper.

26. The process of claim 25 in which said feedstock is dried to a moisture content of from about 9% to about 15% before it is fed into said feed hopper.

27. The process of claim 26 in which said stream of inert gas comprises flue gas.

28. The process of claim 27 in which said flue gas is the exhaust gas from the carbonaceous feedstock reformer into which the comminuted feedstock and steam are fed.

29. The process of claim 24 in which said step of reforming said carbonaceous feedstock is conducted at elevated temperature in a feedstock reformer, and includes adjusting the contact time of the syngas at elevated temperatures in the reformer, and adjusting the exit gas temperature of the syngas as it leaves the reformer, to achieve proportions of carbon monoxide, hydrogen and methane most closely approximating those desired given the intended use of the syngas.

30. The process of claim 29 which includes introducing said feedstock and superheated steam into the feedstock reformer at about 204° C. (400° F.);
adjusting said exit temperature of said syngas leaving said feedstock reformer to between about 871° C. (1600° F.) and about 1204° C. (2200° F.);
adjusting said contact time of said syngas within said reformer within a range of from about 0.4 seconds to about 5.0 seconds.

31. The process of claim 30 in which said catalyzed reactor is catalyzed by a catalyst consisting essentially of elemental cobalt as its primary constituent, with minor amounts of manganese, copper, zinc and one of chromium, aluminum and mixtures thereof.

32. The process of claim 31 in which the catalyst additionally includes an alkali or alkaline earth promoter.

33. The process of claim 32 in which the catalyst consists essentially of from about 65% to about 75% elemental cobalt, about 4% to about 12% manganese, about 4% to about 6% copper, about 4% to about 10% zinc, and about 6% to about 10% of one of chromium, aluminum or mixtures thereof.

34. The process of claim 24 which includes introducing said feedstock and superheated steam into the feedstock reformer at about 204° C. (400° F.);
adjusting said exit temperature of said syngas leaving said feedstock reformer to between about 871° C. (1600° F.) and about 1204° C. (2200° F.);
adjusting said contact time of said syngas within said reformer within a range of from about 0.4 seconds to about 5.0 seconds.

35. The process of claim 34 in which said catalyzed reactor is catalyzed by a catalyst consisting essentially of elemental cobalt as its primary constituent, with minor amounts of manganese, copper, zinc and one of chromium, aluminum and mixtures thereof.

36. The process of claim 35 in which the catalyst additionally includes an alkali or alkaline earth promoter.

37. The process of claim 36 in which the catalyst consists essentially of from about 65% to about 75% elemental cobalt, about 4% to about 12% manganese, about 4% to about 6% copper, about 4% to about 10% zinc, and about 6% to about 10% of one of chromium, aluminum or mixtures thereof.

38. The process of claim 1 in which a portion of said second syngas stream is diverted and used to run a turbine to generate electricity to power compressors and other electrically driven devices used in the process.

* * * * *